(12) United States Patent
Klunder et al.

(10) Patent No.: US 7,851,770 B2
(45) Date of Patent: Dec. 14, 2010

(54) DEVICE FOR OPTICAL EXCITATION USING A MULTIPLE WAVELENGTH ARRANGEMENT

(75) Inventors: Derk Jan Wilfred Klunder, Geldrop (NL); Maarten Marinus Johannes Wilhelm Herpen, Heesch (NL); Marcello Leonardo Mario Balistreri, Rosmalen (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 12/094,788

(22) PCT Filed: Nov. 13, 2006

(86) PCT No.: PCT/IB2006/054223

§ 371 (c)(1),
(2), (4) Date: May 23, 2008

(87) PCT Pub. No.: WO2007/060569

PCT Pub. Date: May 31, 2007

(65) Prior Publication Data

US 2008/0308745 A1 Dec. 18, 2008

(30) Foreign Application Priority Data

Nov. 23, 2005 (EP) .................................. 05111137

(51) Int. Cl.
*G01J 1/58* (2006.01)
(52) U.S. Cl. .................................................. 250/458.1
(58) Field of Classification Search ............... 250/458.1

See application file for complete search history.

(56) References Cited

U.S. PATENT DOCUMENTS

| 6,274,872 B1 * | 8/2001 | Katerkamp ............... 250/458.1 |
| 6,686,208 B2 * | 2/2004 | Meusel et al. ............... 436/518 |
| 2003/0205681 A1 * | 11/2003 | Modlin .................... 250/458.1 |

FOREIGN PATENT DOCUMENTS

| WO | WO0058715 A2 | 10/2000 |
| WO | WO2004059301 A1 | 7/2004 |
| WO | WO2006064465 A2 | 6/2006 |

* cited by examiner

*Primary Examiner*—David P Porta
*Assistant Examiner*—Marcus H Taningco

(57) ABSTRACT

The invention relates to a device for optical excitation, in particular luminescent excitation of biomolecules (40) in a fluid sample, comprising a multiple wavelength generator which generates at least one array of spots (60) with different wavelengths at least one defined area of the device.

13 Claims, 1 Drawing Sheet

DEVICE FOR OPTICAL EXCITATION USING A MULTIPLE WAVELENGTH ARRANGEMENT

The present invention is directed to the field of devices for detection of excitation, especially for evanescent field excitation.

In the field of devices for detection of excitation, especially for evanescent field excitation, which are used e.g. as biosensors, it has been common technique to use a prism, which has an interface with the sample (usually an aqueous medium or other fluid). Into the prism, a single spot or collimated beam of light of a certain wavelength is directed under an angle (with respect to the interface between the prism and the sample) larger than the total internal reflection angle. This results in an evanescent field at the interface with the sample. In case of absorption of the evanescent field by species present in the sample, this can result in the excitation of excited states, which can relax to the ground state by e.g., luminescence resulting in the generation of luminescent radiation. Usually the luminescence is caused by a luminescent, mostly fluorescent-labeled biomolecule such as a protein or a DNA or RNA-strand. The luminescence is then measured and the biomolecule is identified.

However, especially in case that differently labelled biomolecules are present in the sample to be analyzed, prior art solutions require sophisticated layout and tedious analysis techniques.

It is therefore an object of the present invention to provide a device, which allows a quicker detection for samples, especially in the case that differently-labeled analytes are present.

This object is solved by a device according to claim 1 of the present invention.

Accordingly, a device for detecting excitation, in particular luminescent excitation in a fluid sample is provided comprising a multiple wavelength generator, which generates at least one array of spots where different array of spots have different wavelengths at least one defined area of the device.

By doing so, the following advantages can be achieved for most applications:

- In case different luminophores (like fluorophores) are used for the detection device, these luminophores can be detected more efficient, especially time-efficient and with a higher resolution
- A device according to the present invention allows a quick high-throughput screening, especially for labeled biomolecules
- A device according to the present invention allows an improved flexibility, because the multiple wavelength generator generates a comb (not necessarily at constant wavelength spacing) of excitation wavelengths. For fluorescence, the excitation spectra (fluorescent signal as a function of the excitation wavelength) have a spectral width of typically 10-50 nm. This implies that a multiple wavelength generator with a wavelength-spacing between subsequent wavelengths for which the multiple wavelength generator operates properly smaller than the spectral width of the excitation spectra of the luminophores can be used for the excitation of any luminophore (with sufficiently wide excitation spectrum, i.e. bandwidth larger than spacing between subsequent wavelengths) whose excitation wavelength is within the minimum and maximum wavelength for which the multiple wavelength generator operates properly.

According to a preferred embodiment of the present invention the device furthermore comprises a transparent slab or slab substrate having a slab-sample interface and the array of spots is provided on or in the vicinity of the slab-sample interface.

By using such a device, one or more—depending on the actual application—of the following advantages can be reached:

- The conversion of excitation power into evanescent waves is more efficient than in prior art solution; i.e., more power per spot compared with arrangement with mask with blocks and because that maximum useful power per spot is limited by saturation effects dividing the power over multiple spots results in more efficient use of the total power.
- The optical paths of the excitation light (which is the light that enters the slab) and the luminescence (which is the light that is emitted by the sample) are better separated
- The device is usually simpler than those of the prior art
- The device does not require synchronization of multiple spot arrangement with other optical elements (like a mask used for blocking).

The term "slab" in the sense of the present invention means especially a cuboid or prism-shaped device, which allows a multiple spot arrangement to be formed at an interface between the slab and the sample. According to a preferred embodiment, the slab is a prism; however, for other applications it may be preferred that the slab is cuboid-shaped.

The term "transparent" in the sense of the present invention means especially that the material is essentially transparent (sufficiently low losses) for light having the excitation wavelength and/or the luminescent wavelength.

The term "slab-sample interface" in the sense of the present invention means especially that at least one side of the slab is exposed to the excitation light or is directed towards the sample. This side is then called the interface. In case that surface plasmon resonance is used (as will be described below), there may be a surface plasmon layer provided between the slab and the sample. The "slab sample interface" is then provided with the side of the surface plasmon layer projecting towards the sample.

According to a preferred embodiment of the present invention, the wavelengths of the at least one array of spots are from $\geq 200$ nm and $\leq 2000$ nm; according to an embodiment of the present invention, the wavelengths of the at least one array of spots are from $\geq 300$ nm to $\leq 800$ nm.

According to a preferred embodiment of the present invention, the average difference in wavelength within between adjacent (in terms of wavelength) arrays is $\geq 5$ nm and $\leq 150$ nm; according to a preferred embodiment of the present invention, the average difference in wavelength between adjacent (in terms of wavelength) arrays of spots is $\geq 10$ nm and $\leq 100$ nm; according to a preferred embodiment of the present invention, the average difference in wavelength is $\geq 50$ nm to $\leq 75$ nm.

According to a preferred embodiment of the present invention, the average deviation in the average difference in wavelength within between adjacent (in terms of wavelength) arrays is $\geq 0$ nm and $\leq 20$ nm; according to a preferred embodiment of the present invention, the average deviation in the average difference in wavelength within between adjacent (in terms of wavelength) arrays is $\geq 3$ nm and $\leq 15$ nm; according to a preferred embodiment of the present invention, the average deviation in the average difference in wavelength between adjacent (in terms of wavelength) arrays is $\geq 5$ nm and $\leq 10$ nm.

According to an embodiment of the present invention, the multiple wavelength generator comprises at least one polarization device so that at least one of the spots of the at least one array of spots comprises polarized light. For most applications this has the advantage that reflected light may be blocked by a blocking means, as will be described later on.

According to an embodiment of the present invention, the multiple wavelength generator comprises at least one polarization filter that transmits one polarization state (ps1) and does not transmit or reflect another (orthogonal) polarization state (ps2);

According to an embodiment of the present invention, the multiple wavelength generator comprises at least one polarization rotator which rotates the polarization state by a rotation angle of $\delta\phi 1$ degrees.

According to a preferred embodiment of the present invention, the multiple wavelength generator comprises a blocking means which blocks the light or parts thereof generated by the multiple wavelength generator.

According to a preferred embodiment of the present invention, the multiple wavelength generator comprises a first blocking means which blocks one polarization component (polarization state 2; ps2) of the light generated by the multiple wavelength generator and transmits the other polarization component (polarization state 1; ps1) and a second blocking means which blocks the light reflected by at the slab-sample interface.

According to an embodiment of the present invention, the blocking means comprises a polarization filter and/or a polarization rotator.

According to an embodiment of the present invention, the blocking means comprises at least one polarization rotator that rotates the polarization state by $\delta\phi 2$ degrees such that $|\delta\phi 1+\delta\phi 2|=90$ degrees is fulfilled.

According to an embodiment of the present invention, the polarization device polarizes the device to p/s polarized light and the blocking means blocks p/s polarized light and/or the polarization device polarizes the device to s/p polarized light and the blocking means blocks s/p polarized light.

According to an embodiment of the present invention, the device comprises a first blocking means which comprises a polarization filter that blocks polarization state ps2 and/or a polarization rotator that rotates the polarization angle by $\delta\phi 1$ degrees and a second blocking means which comprises a polarization filter and/or a polarization rotator that rotates the polarization angle by $\delta\phi 2$ degrees. According to an embodiment of the present invention, the polarization rotators are configured such that $|\delta\phi 1+\delta\phi 2|=90$ degrees is fulfilled.

According to an embodiment of the present invention, the spatial distributions of the array of spots of different wavelengths are essentially overlapping; i.e., the centre positions for adjacent spots of different wavelengths do not deviate more than +/−15%, according to one embodiment of the present invention not more than +/−10% of the average pitch between subsequent spots of the same wavelength.

According to a preferred embodiment of the present invention, the slab is a prism having a prism-sample interface with angles such that incident excitation light is totally internally reflected on a prism-sample interface and whereby preferably the angle of the prism $\phi$ is selected to be as follows:

$$\theta_{TIR} \leq \phi \leq \frac{\pi}{2}$$

with $\theta_{TIR}$ being the total internal reflection angle as the minimum angle with respect to the normal of the interface that results in total internal reflection:

$$\theta_{TIR} = \arcsin\left(\frac{n_{sample}}{n_{prism}}\right)$$

According to a preferred embodiment of the present invention, the total internal reflection cone $\phi$ of the slab is $$\theta_{TIR} \leq \phi \leq \frac{\pi}{2}$$

A device according to the present invention may be of use in a broad variety of systems and/or applications, amongst them one or more of the following:

biosensors used for molecular diagnostics rapid and sensitive detection of proteins and nucleic acids in complex biological mixtures such as e.g. blood or saliva high throughput screening devices for chemistry, pharmaceuticals or molecular biology testing devices e.g. for DNA or proteins e.g. in criminology, for on-site testing (in a hospital), for diagnostics in centralized laboratories or in scientific research tools for DNA or protein diagnostics for cardiology, infectious disease and oncology, food, and environmental diagnostics tools for combinatorial chemistry analysis devices.

The aforementioned components, as well as the claimed components and the components to be used in accordance with the invention in the described embodiments, are not subject to any special exceptions with respect to their size, shape, material selection and technical concept such that the selection criteria known in the pertinent field can be applied without limitations.

BRIEF DESCRIPTION OF THE DRAWINGS

Additional details, features, characteristics and advantages of the object of the invention are disclosed in the subclaims, the figures and the following description of the respective figures and examples, which—in an exemplary fashion—show several preferred embodiments of a device according to the invention.

FIG. 1 shows a very schematic cross-sectional view of a device 1 according to a first embodiment of the present invention. The device comprises a slab 10 in form of a prism, which has an interface 20 with the sample 30. The sample 30 is an aqueous or fluidic medium, in which luminescent, preferably fluorescent-marked biomolecules 40 are present.

Figure 1:
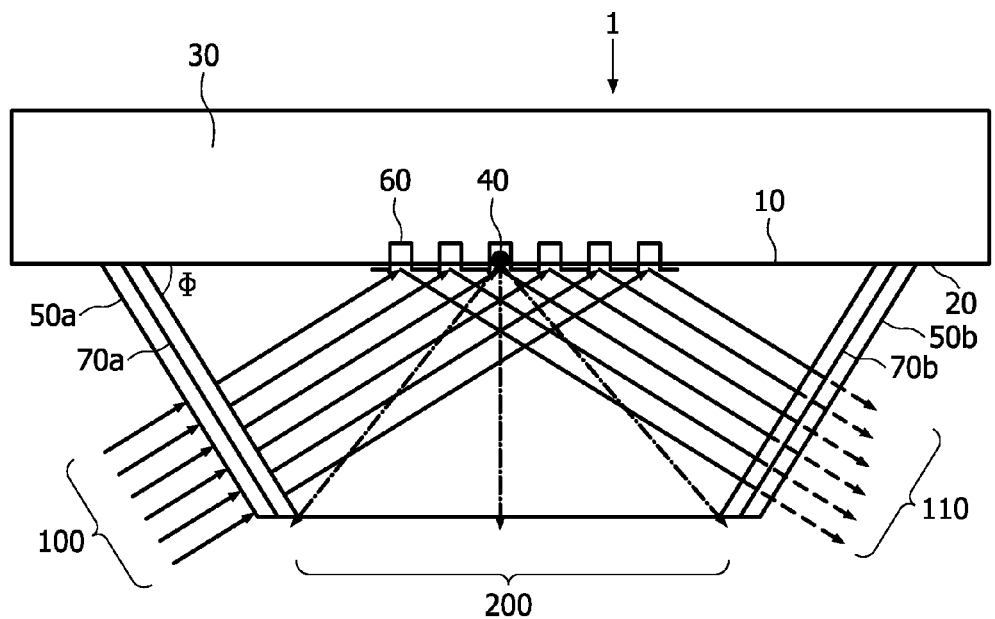
FIG. 1 shows a very schematic cross-sectional view of a device according to a first embodiment of the present invention.

The device furthermore comprises a multiple wavelength generator in form of two diffraction elements 50a and 50b. The diffraction element 50a is a phase plate which generates an array of spots 60 having a wavelength λ1. The diffraction element 50b is a phase plate which generates an array of spots having a wavelength λ2. It should be noted that in FIG. 1 only the way of the light 100 with wavelength λ1 (from left to right) is shown; the way of the light with wavelength λ2 is similar (from right to left), but not shown in FIG. 1 for clarity reasons.

The light 100, after passing through the first diffraction element 50a, passes a blocking means 70a in the form of a polarization filter that transmits one polarization state (ps1) and does not transmit or reflect the other (orthogonal) polarization state (ps2); light having polarization state ps2 is absorbed by the polarization filter. Subsequently, the light enters a polarization rotator which rotates the polarization state by a rotation angle of δφ1 degrees.

In case that a biomolecule 40 is present in the evanescent part of the multiple spot arrangement, fluorescent light (as indicated by the dotted lines 200) is emitted and may be detected, thus indicating the presence of the biomolecule 40 in the sample 30.

However, most of the light 100 will be reflected (numeral 110) towards the second diffraction element 50b and the second blocking means 70b. This second blocking means 70b also comprises a polarization rotator that rotates the polarization state by δφ2 degrees such that |δφ1+δφ2|=90 degrees. As a result the light has the polarization state ps2 after passing the polarization rotator. Subsequently, the light enters a polarization filter that transmits ps1 and absorbs ps2.

In order to distinguish the fluorescent light 200 from the incident light 100 and reflected light 110 which is not blocked by the blocking means 70b, the angle φ of the slab 10 and the total cone of reflection are chosen to be as described above.

The second diffraction element 50b generates an array of spots with a wavelength λ2 (not shown in the fig). Since, after passing through the blocking means 70b, the light has a polarization angle of δφ2 degrees relative to the ps1, the light reflected by the slab 10 will be blocked by the blocking means 70a (which rotates the polarization state of the reflected light by δφ1 degrees and blocks polarization state ps2).

Therefore, the blocking means 70a blocks light from the diffraction element 50b and vice versa blocking means 70b blocks light from the diffraction element 50a; thus the blocking means 70a serves as polarization means for the blocking means 70b and vice versa.

Figures 2A, 2B:
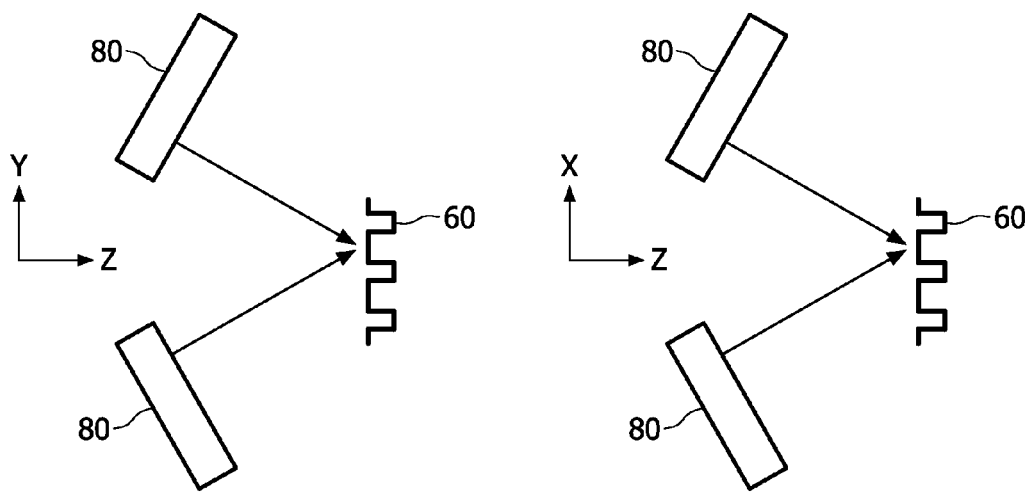
FIGS. 2 a and b show schematic views of a device according to a second embodiment of the present invention seen from the y-z- and x-z axis.

FIGS. 2a and b show very schematic views of a device according to a second embodiment of the present invention seen from the y-z- and x-z axis. In this device, four wavelength generators 80 are present, each generating an array of spots 60 with different wavelengths, similar to FIG. 1. These wavelength generators 80 are provided somewhat "three-dimensional" as indicated by the Y-Z and X-Z axis in FIGS. 2a and 2b respectively.

It goes without saying that the present invention is not only of use in devices using evanescent fields but also in devices using propagation waves. A device like this is shown in the EP04106680.4, which is hereby fully incorporated by reference.

The particular combinations of elements and features in the above detailed embodiments are exemplary only; the interchanging and substitution of these teachings with other teachings in this and the patents/applications incorporated by reference are also expressly contemplated. As those skilled in the art will recognize, variations, modifications, and other implementations of what is described herein can occur to those of ordinary skill in the art without departing from the spirit and the scope of the invention as claimed. Accordingly, the foregoing description is by way of example only and is not intended as limiting. The invention's scope is defined in the following claims and the equivalents thereto. Furthermore, reference signs used in the description and claims do not limit the scope of the invention as claimed.

The invention claimed is:

1. A device for detecting luminescent excitation in a fluid sample, the device comprising:
   a multiple wavelength generator that generates arrays of spots having different corresponding wavelengths at at least one defined area of the device, the multiple wavelength generator comprising a plurality of spot array generators corresponding to the arrays of spots and at least one blocking element configured to block reflected light from at least one of the spot array generators,
   wherein a first blocking element comprises a first polarization filter that blocks polarization state ps2 and a first polarization rotator that rotates a polarization angle by δφ1 degrees, and wherein a second blocking element comprises a second polarization filter and a second polarization rotator that rotates a polarization angle by δφ2 degrees.

2. The device according to claim 1, further comprising:
   a transparent slab having a slab-sample interface, wherein the arrays of spots are provided on or near the slab-sample interface.

3. The device according to claim 2, wherein the slab comprises a prism and the slab-sample interface has angles such that incident excitation light is totally internally reflected on the slab-sample interface, and wherein an angle of the prism φ is selected to be as follows:

$$\theta_{TIR} \le \phi \le \frac{\pi}{2}$$

with $\theta_{TIR}$ being a total internal reflection angle, which is the minimum angle with respect to a normal of the slab-sample interface that results in total internal reflection:

$$\theta_{TIR} = \arcsin\left(\frac{n_{sample}}{n_{prism}}\right).$$

4. The device according to claim 2, wherein a total internal reflection cone φ of the slab is $$\theta_{TIR} \le \phi \le \frac{\pi}{2}$$

with $\theta_{TIR}$ being a total internal reflection angle, which is the minimum angle with respect to a normal of the slab-sample interface that results in total internal reflection:

$$\theta_{TIR} = \arcsin\left(\frac{n_{sample}}{n_{prism}}\right).$$

5. The device according to claim 1, wherein the wavelengths of the arrays of spots are from ≧200 nm to ≦2000 nm.

6. The device according to claim 1, wherein an average difference in wavelength between arrays of spots that are adjacent in terms of wavelength is ≧5 nm and ≦150 nm.

7. A system incorporating the device according to claim 1, and being used in one or more of the following applications:
   biosensors used for molecular diagnostics;
   rapid and sensitive detection of proteins and nucleic acids in complex biological mixtures;

high throughput screening devices for chemistry, pharmaceuticals or molecular biology;

testing devices for DNA or proteins;

tools for DNA or protein diagnostics for cardiology, infectious disease and oncology, food, and environmental diagnostics;

tools for combinatorial chemistry; and analysis devices.

8. A device for detecting luminescent excitation in a fluid sample, the device comprising:

a transparent slab comprising an interface with the fluid sample;

a first diffraction element that receives incident light and generates a first array of spots having a first wavelength at the interface;

a second diffraction element that receives incident light and generating a second array of spots having a second wavelength at the interface, the second wavelength being different from the first wavelength;

a first blocking element between the first diffraction element and the slab, the first blocking element comprising a first polarization filter and a first polarization rotator; and a second blocking element between the second diffraction element and the slab, the second blocking element comprising a second polarization filter and a second polarization rotator, wherein the second blocking element blocks first light from the first diffraction element reflected by the slab, and the first blocking element blocks second light from the second diffraction element reflected by the slab.

9. The device of claim 8, wherein the slab comprises a prism.

10. The device of claim 9, wherein the first and second polarization filters transmit a first polarization state.

11. The device of claim 8, wherein the first polarization rotator rotates a polarization state by a rotation angle of df 1 degrees and the second polarization rotator rotates a polarization state by a rotation angle of df 2 degrees, wherein |df1+df2|=90 degrees.

12. The device according to claim 8, wherein each of the first and second wavelengths is from $\geq 200$ nm to $\leq 2000$ nm.

13. The device according to claim 8, wherein the first and second wavelengths are adjacent in terms of wavelength and have a difference in wavelength $\geq 5$ nm and $\leq 150$ nm.

* * * * *